United States Patent [19]

Amor et al.

[11] Patent Number: 4,658,408
[45] Date of Patent: Apr. 14, 1987

[54] COMPUTED TOMOGRAPHY BRAKE METHOD AND APPARATUS

[75] Inventors: William H. Amor, Chagrin Falls; Robert E. Levar, Willoughby, both of Ohio

[73] Assignee: Picker International Inc., Highland Heights, Ohio

[21] Appl. No.: 707,732

[22] Filed: Mar. 4, 1985

[51] Int. Cl.$^4$ ............................................. G01N 23/00
[52] U.S. Cl. ........................................... 378/4; 378/20; 188/82.2; 188/82.3; 188/166; 318/375
[58] Field of Search ....................................... 378/4–20; 188/82.2, 82.3, 82.4, 110, 166; 318/373, 375

[56] References Cited

U.S. PATENT DOCUMENTS

| | | | |
|---|---|---|---|
| 1,408,929 | 3/1922 | Clay | 188/82.3 |
| 2,945,998 | 7/1960 | Vanderberg | 318/373 |
| 3,094,195 | 6/1963 | Lund | 188/82.2 |
| 4,088,888 | 5/1978 | Brook et al. | |
| 4,112,303 | 9/1978 | Brandt | |
| 4,187,429 | 2/1980 | Tomita et al. | |
| 4,366,577 | 12/1982 | Brandt | 378/4 |
| 4,426,578 | 1/1984 | Bradcovich et al. | 378/15 |
| 4,546,297 | 10/1985 | Washbourn et al. | 318/273 |

Primary Examiner—Craig E. Church
Assistant Examiner—John C. Freeman
Attorney, Agent, or Firm—Watts, Hoffman, Fisher & Heinke Co.

[57] ABSTRACT

A computed tomography scanner having a brake which is automatically engaged in the event dynamic motor braking fails to stop scanner motion. Within a predetermined range of motion two brake mechanisms are employed. One has a brake shoe to contact a braking surface and stop rotation of the scanner in one direction and a second has a second brake shoe which stops rotation in an opposite direction. The brake shoes are engaged and retracted by a cam surface which as the scanner rotates, moves into contact with one of two bearings connected to associated ones of the brake shoes.

10 Claims, 11 Drawing Figures

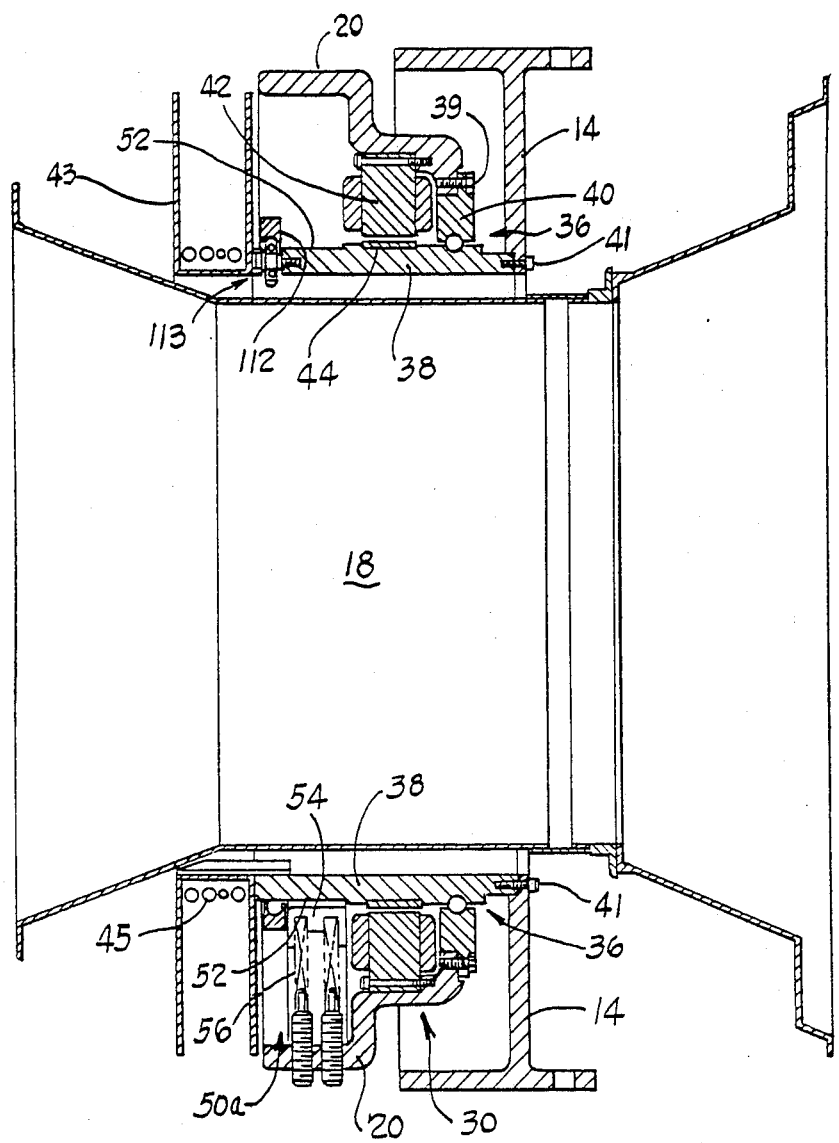
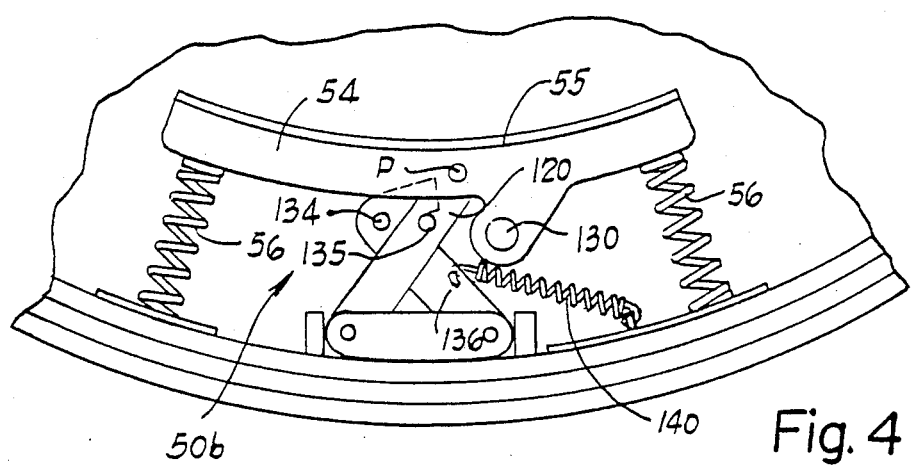

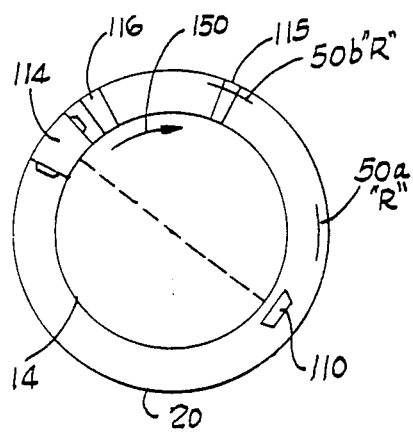
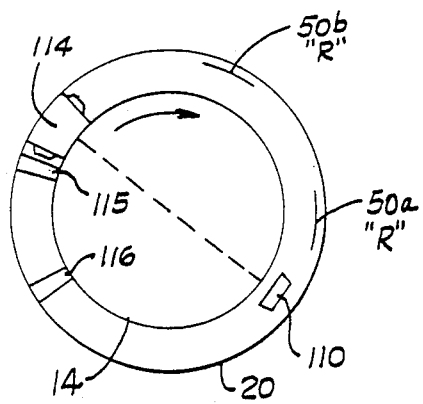
Fig. 5A          Fig. 5B
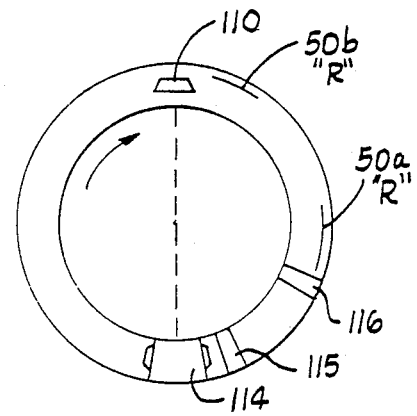
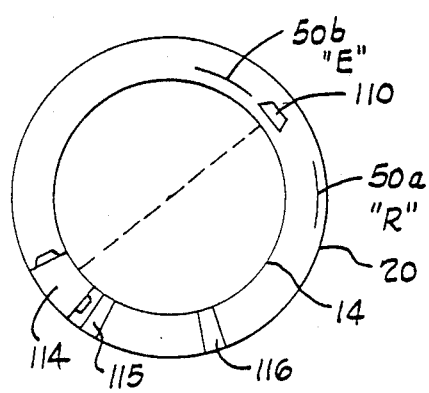
Fig. 5C          Fig. 5D
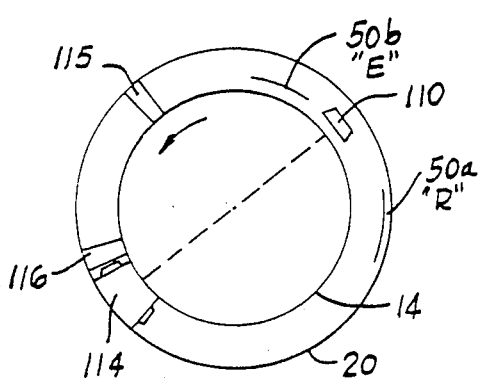
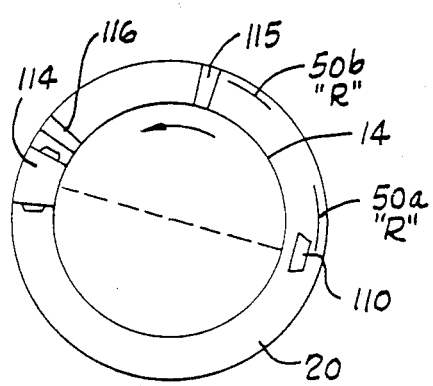
Fig. 5E          Fig. 5F
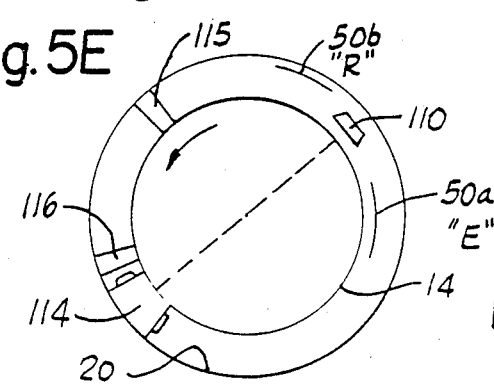
Fig. 5G

COMPUTED TOMOGRAPHY BRAKE METHOD AND APPARATUS

TECHNICAL FIELD

The present invention relates to a brake mechanism particularly suited for use in a computed tomography scanner.

BACKGROUND ART

In transmission computed tomography, a patient or subject cross-section of interest is successively scanned from a number of directions by an x-radiation source to direct X-rays through a cross-section of interest. One or more detectors positioned on an opposite side of the patient obtain intensity readings of the x-radiation after it has passed through the patient. If enough intensity measurements from different directions are obtained, these intensity readings can be utilized to reconstruct a density mapping of the patient cross-section.

Computed tomography reconstruction techniques are derived from mathematical reconstruction algorithms utilizing the fact that each radiation intensity reading corresponds to a line integral of an attenuation function taken through the patient cross-section from the source to the position the intensity is sensed. These reconstruction algorithms allocate this attenuation along the path the radiation takes in traversing the patient in a process known as back projection.

Fourth generation computed tomography designs include an array of stationary detectors and a moving x-radiation source. The fourth generation array of detectors typically surrounds a patient aperture which defines a patient scanning plane. An X-ray source then radiates the plane from a number of different directions. This scanning is typically achieved by orbiting an X-ray tube about the patient and detecting X-ray intensities of radiation passing through the patient.

In early computed tomography scanner designs the detectors also moved as the patient was scanned. In orbital CT designs, for example, the X-ray source and an arc of detectors orbit in unison about the patient.

A common need in all commercial transmissive computed tomography scanners known to applicants is a motive force for moving at least the X-ray source and in some designs both the source and detectors. A motor for rotating the X-ray source must be capable of applying a large torque to a fairly large X-ray gantry to accelerate the gantry in a short time to a constant rate of rotation.

In currently available CT equipment such as a fourth generation CT scanner designated the Synerview 1200 which is commercially available from Picker International, Inc. of Cleveland, Ohio, the rotating CT apparatus defines an aperture of sufficient diameter to allow a patient torso to be inserted for scanning. Since the inertia of any rotational apparatus increases with distance from the axis of rotation, provision for full body scanning capability results in rotating apparatus (including an X-ray tube) having a large inertia.

When a Synerview 1200 or other scanner is used, a motor is energized, a scan taken and motion stopped. Typically, the direction of rotation is then reversed and a second scan is taken. The direction of scan rotation alternates back and forth so that only a finite angle of scanning motion is traversed each scan.

The scanning apparatus requires a braking force be applied after each CT scan and because of the high inertia, the required force is large. The Synerview 1200 scanner uses dynamic braking by reverse energizing its motor. Shock absorbing stops in the Synerview 1200 limit the travel of the CT rotating frame in the event the dynamic braking fails or is inadequate. Without the shock absorbing stops the cabling leading to the high voltage X-ray tube will be damaged in the event of a failure of dynamic braking to stop scanning motion.

DISCLOSURE OF INVENTION

The invention relates to a brake mechanism particularly suited for use in a CT scanner. The brake mechanism includes a brake shoe and friction surface which are designed to stop CT scanning motion. The disclosed brake applies lower braking forces for longer periods of time than shock absorbing stops of the prior art. An advantageous feature of the invention is that as the brake shoe wears with use, the braking force applied to the scanning apparatus remains relatively constant.

The brake mechanism of the invention includes a brake shoe supported by a stationary structure for movement between a braking position and non-braking position. A lever arm pivotally couples the brake to the stationary structure and a biasing mechanism such as a spring or the like urges the brake against a friction surface when the brake is applied. The brake is retained in the non-braking position and selectively released by a cam surface movable with respect to the stationary structure.

In a preferred embodiment, the brake is used as an emergency brake to stop motion of CT scanner frame. A motor drives the source in one direction as a first CT scan takes place. After this scan is completed, the motor is reverse energized to stop scanner rotation. This dynamic braking action is supplemented by the brake mechanism if the dynamic braking fails to stop scanner movement. The brake mechanism can provide all the braking action to stop the rotating frame even if the dynamic braking never occurs and the motor is in a "run away" state.

Under normal scanning conditions, once scanner movement stops the motor is re-energized to scan in an opposite sense. During reverse scanning the brake mechanism is automatically disengaged by action of the cam surface. To accomodate the two direction scanning requirements, the preferred CT scanner includes two brake mechanisms.

Brake engagement and retraction are accomplished by a cam surface which sequentially contacts two contact pins on each brake mechanism. As the cam surface moves past the brake mechanism in one direction a brake shoe having a brake pad is retracted by contact with a first pin and held in place in a retracted condition by a second pin connected to a retaining arm.

In an opposite direction, the cam surface first contacts the second pin to move the retaining arm. As the cam surface continues to move, it contacts the first pin to release the brake shoe and allow springs to bias the shoe against the friction surface.

Each brake mechanism is self actuating and is configured such that wear of its brake pad does not significantly alter braking action. As the brake pad wears the spring biasing force is reduced but the force of coaction between the lever arm and brake pad increases so that the normal force the pad exerts on the friction surface decreases only slightly.

One object of the invention is a new and improved self actuating brake mechanism, particularly suited for a CT scanner, that exerts uniform stopping action over its useful life even as the brake pads wear. Other objects, advantages, and features of the invention will become better understood as a preferred embodiment of a structure embodying the invention is described in conjunction with the accompanying drawings.

BRIEF DESCRIPTION OF THE DRAWINGS

FIG. 3 is a sectional view of the structure of FIG. 2 as seen from a plane indicated by line 3—3 in FIG. 2;

FIG. 4 is an enlarged elevation view of an emergency brake mechanism; and

FIGS. 5A-5G are schematic representations of the FIG. 1 scanner showing different orientations of a rotating frame in relation to a scanner gantry.

BEST MODE FOR CARRYING OUT THE INVENTION

Figure 1:
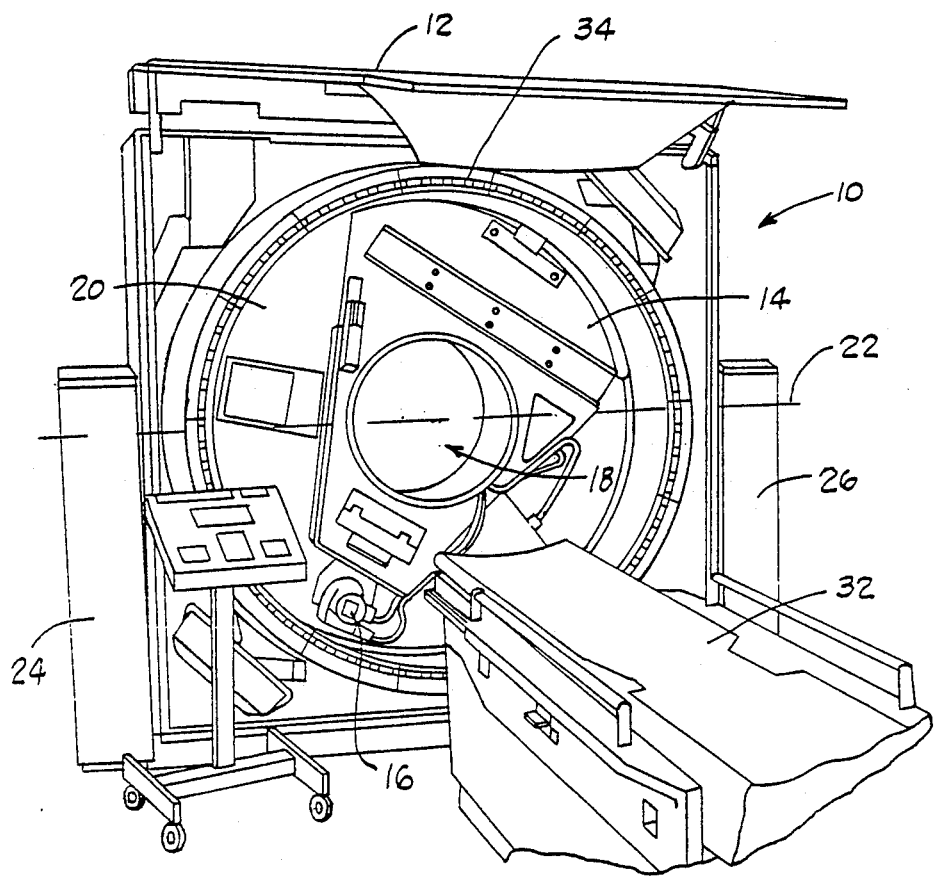
FIG. 1 is a perspective view of a computed tomography scanner.

Referring to the drawings and in particular to FIG. 1, a computed tomography scanner 10 is illustrated. In the FIG. 1 representation a scanner housing cover 12 has been pivoted away from its normal in use position to illustrate certain components of the scanner. A scanning frame 14 supports an X-ray tube 16 for rotation about a patient aperture 18. The frame 14 is rotatably mounted to a gantry 20 and the entire gantry and accompanying frame can be pivoted about a horizontal axis 22 passing through the patient aperture. Two vertical supports 24, 26 support the gantry and rotatable frame for this tilting motion.

During scanning, a motor 30 (FIG. 3) causes relative movement between the frame 14 and gantry 20 to cause the frame mounted X-ray tube 16 to traverse a circular or orbital path about the aperture 18. During scanning a patient is positioned on a couch 32 and then is inserted into the patient aperture 18 so that a particular patient slice of interest can be scanned.

A generally planar spread beam of radiation originating from the X-ray tube 16 impinges upon a number of detectors in a circular detector array 34. In the disclosed design, the detectors completely circumscribe the patient so that regardless of the orientation of the X-ray tube 16, a certain percentage of the detectors surrounding the patient aperture are sensing radiation intensity during scanning. Sensed radiation intensity information is utilized in one of a number of known reconstruction processes to create a cross-sectional image of the patient slice of interest.

The cross-sectional view of FIG. 3 further illustrates the relationship of these computed tomography scanner components in relation to the patient aperture 18. While the X-ray tube and detectors are not seen in this FIGURE, a coupling between the stationary gantry 20 and rotating frame 14 is seen. A large circumference bearing 36 having inner 38 and outer 40 races circumscribes the patient aperture and is coupled to the stationary gantry 20 by threaded connectors 39. The rotating frame is connected to the inner race by similar threaded connecters 41 which engage tapped holes located at one end of the inner race 38.

The motor 30 is a variable speed three phase induction type motor having energizable windings 42 coupled to the gantry. A number of magnets 44 are coupled to the inner race 38 and interact with magnetic fields generated by the windings 42. Selective energization of the windings creates electromagnetic fields to which the magnets respond and cause relative rotation between the gantry and frame.

As the frame 14 is rotated, high voltage cabling 45 winds and unwinds from a cable take up 43 supported by the inner race 38. This cabling 41 that will be damaged if relative rotation is not stopped after failure of dynamic braking.

At the conclusion of a computed tomography scan, the X-ray tube 16 is de-energized and the electromagnetic motor is reverse energized to produce dynamic braking. This dynamic breaking typically results in a complete cessation of movement between gantry and frame in an arc of approximately 30 degrees of frame rotation.

Figure 2:
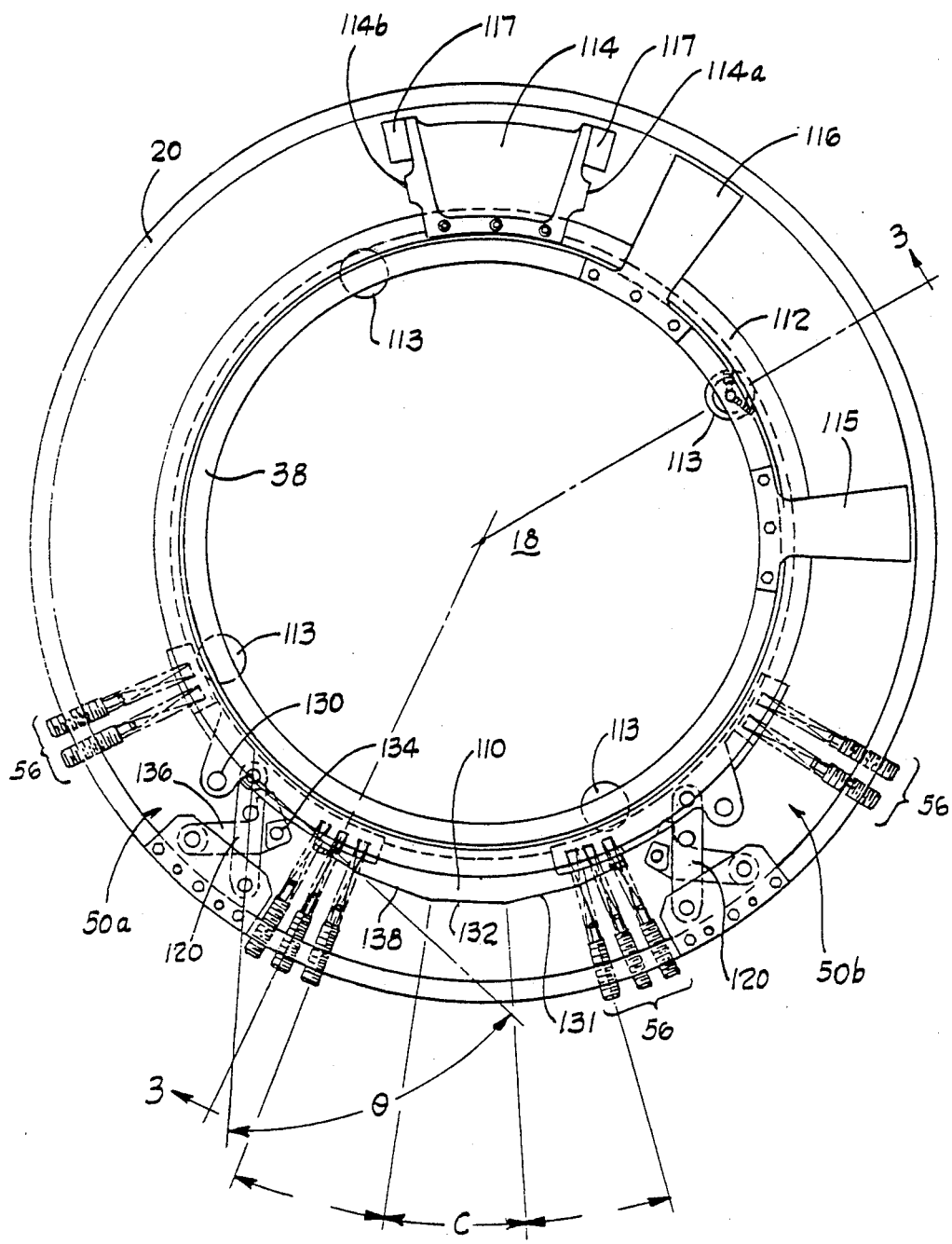
FIG. 2 is a front elevational view of a portion of a stationary gantry with a back cover removed shown supporting a rotating frame which in turn supports a scanning X-ray source.

Two emergency brake mechanisms 50a, 50b (FIG. 2) connected to the gantry 20 are provided to stop relative rotation in the event of a failure of the dynamic braking. The brake mechanisms 50a, 50b are designed to stop frame rotation even if the motor 30 is not reverse energized but instead continues to drive the frame in the same direction as a just completed scan.

The brake mechanisms 50a, 50b are designed to provide a more gradual braking action than the shock absorbers used as stops in the prior art. The mechanisms are also designed to be actuated automatically by relative rotation between the frame 14 and the gantry 20 in a way such that only one of the two brake mechanisms 50a, 50b is actuated at a given time depending upon the direction of frame rotation at the time dynamic braking fails to stop the frame.

The bearing inner race 38 defines an outwardly facing braking surface 52 (FIG. 3). If either brake mechanism is actuated this surface 52 is frictionally engaged by a brake shoe 54 of that mechanism having a brake pad 55 (FIG. 4). The preferred mechanism for applying a normal force between the brake shoe 54 and the surface 52 are sets of compressed springs 56. Each spring set directs an inward force against an associated one of the brake shoes 54.

A cam 110 connected to a rotatable ring 112 engages and disengages the two brake mechanisms 50a, 50b. The ring 112 is supported by four bearings 113 equally spaced about a face of the inner bearing race 38. The bearings 113 allow the ring 112 to rotate relative to the frame 14. A cam operator 114, also coupled to the ring 112, drives the cam 110 past the brake and depending on its direction of movement either engages or disengages one of the brake mechanisms.

The cam operator 114 extends in a radial direction outwardly from the ring 112 and defines two contact surfaces 114a, 114b. These surfaces 114a, 114b are engaged by two drive arms 115, 116 mounted to the frame. Foam stops 117 mounted to the cam operator 114 absorb the shock of contact between the arms 115, 116 and the metal contact surfaces 114a, 114b. In a preferred embodiment the arms 115, 116 are coupled to the inner bearing race 38 but could alternately be coupled to or from a part of the cable take up 43. In combination, the arms 115, 116, cam operator 114, and rotatably supported ring 112 comprise a lost motion mechanism whereby greater than 360° of frame rotation occurs prior to brake mechanism actuation.

Each brake shoe 54 is held in position by a connecting rod 120 which forms an angle θ with respect to a tangent line to the outside diameter of the braking surface 52. This angle creates a self-locking force, $F_L$, which drives the shoe 54 into the surface when the brake mechanism 50b shown in FIG. 4 is actuated by clockwise rotation of the frame 14. Conversely, coaction between the brake shoe 54 of the mechanism 50b and the brake surface 52 drives the shoe 54 away from the surface 52 when the frame 14 (and brake surface 52) is rotating in a counterclockwise sense. Thus, the brake mechanism 50b will stop the frame from rotating in a clockwise direction yet allow the motor 30 to backdrive the frame 14 in the counterclockwise direction.

Each spring set 56 drives its associated shoe 54 into the surface 52 with a force $F_s$. The total force N driving the shoe pad 55 against the surface 52 is $N = F_s \pm F_L = F_s \pm u \tan\theta N$, where u is the co-efficient of dynamic friction of the brake pad material on the surface 52. In one embodiment this co-efficient is 0.55. The force is selected such that an actuated brake mechanism stops the frame within an 11° to 30° angle when the frame is rotating at 60 revolutions per minute. It is undesirable to stop in less than 11° because the G forces are excessive. More than 30° may damage the electrical cables 41 going to the frame. Ideally, maximum available rotation should occur before stopping to minimize the G forces. With the force N set at 1400 lb. brake mechanisms 50a, 50b will stop the frame in 27° of rotation if actuated as the frame rotates at 60 revolutions per minute.

The angle θ is not a constant, but increases as the brake pad 55 wears. This increase in θ increases the self locking force $F_L$. The initial angle θ is selected such that as the brake pad wears and reduces the spring force $F_s$ due to extension of the springs, the force $F_L$ increases to keep the total force N approximately the same.

In actual practice, the initial angle θ is selected so that the total force N increases slightly as brake pad wear occurs. Thus, under a given set of rotational conditions the frame will be stopped in a smaller angle by a worn brake pad. This permits the brake system to be adjusted and set for maximum travel at the factory with the knowledge that as the system wears with use it will still not allow the frame 14 to stop in more than 30°.

Each connecting rod 120 is connected to its associated shoe at a point P, above the braking surface. This causes a moment M about point P when the shoe is engaged. The spring sets 56 are purposely unbalanced to compensate for this moment M and thus maintain a constant force over the length of the brake pad contact face when the brake is actuated.

Each of the brake mechanisms 50a, 50b is actuated and reset by the cam 110. Cam movement is accomplished by the cam operator 114 which rotates the ring 112 in response to movement of two drive arms 115, 116 which are connected to and rotate with the inner race. As the frame is rotating in the counterclockwise direction, the arm 116 contacts the cam operator surface 114a to rotate the cam 110 into engagement with a bearing 130 attached to the brake mechanism 50a and drives its brake shoe 54 away from the brake surface as the bearing 130 rides up a cam face 131. As the bearing 130 dwells on a top cam face 132, a bearing 134 on a lock dog 136 rides up the cam face 131. This disengages the lock dog 136 from a pin 135 extending from the connecting rod 120. The dwell length C is the same as the distance between the bearings 130, 134. As the bearing 130 rides down a third cam face 138 engaging the brake shoe 54 on the braking surface 52, the lock dog 136 is held disengaged from the connecting rod 120 by the bearing 134 riding on the cam face 132. When so engaged the frictional force between the surface 52 and the brake pad 55 will stop rotation before the cam 110 reaches the second brake mechanism 50b.

The brake mechanism 50a is reset by driving the cam 110 past the brake mechanism 50a in a clockwise sense. The lock dog bearing 134 rides up the cam face 138 and dwells on the cam face 132 as the brake shoe bearing 130 rides up the cam face 138 disengaging the brake shoe 116 from the surface 52. As the lock dog bearing rides down the cam face 131 the lock dog 136 is pulled into engagement with the connecting rod pin 135 by a spring 140 (FIG. 4). As the brake shoe bearing 130 rides down the cam face 131, the lock dog holds the shoe 116 disengaged from the surface 52. The cam faces 131, 138 are designed symmetrically so that the cam can actuate the second brake mechanism 50b (FIG. 4) to stop the frame at the end of a clockwise scan.

Referring now to FIGS. 5A-5G, a sequence of brake, frame, and gantry positions are schematically indicated to illustrate operation of the system of the invention. This sequence illustrates the lost motion aspects of cam operator movement and self-actuating feature of brake operation.

In FIG. 5A, each brake mechanism 50a, 50b is in a retracted position away from the braking surface. In the FIG. 5A representation the frame 14 has been stopped by the dynamic braking action of the motor 30. FIG. 5A indicates that scanning motion is to begin in a direction of an arrow 150 by controlled energization of the motor windings. Neither brake mechanism is actuated although it is apparent that previous scanning motion has brought the cam 110 nearly to the position of one of brake mechanisms 50a.

Turning now to FIG. 5B, the motor is energized and scanning begins to occur. Initially, the cam 110 does not move. The rotating frame 14 drives the two arms 115, 116 until the arm 115 contacts the cam operator 114. This contact is achieved after approximately 270° of frame rotation. Subsequent to this contact, the arm 115 moves the cam operator 114, the ring 112, and the cam 110.

FIG. 5C shows the relationship between the frame 14 and the gantry 20 after clockwise rotation of the frame 14 has caused the arm 115 to move the cam operator 114 from its position in 5B until the cam 110 is about to actuate the brake mechanism 50b. The total amount of scanning movement experienced by the frame 14 in FIGS. 5A-5C is 458°. This 458° includes 30° to accelerate the frame, 398° of x-ray scanning, and 30° to dynamically brake and decelerate the frame. If the dynamic braking action of the motor has stopped the frame, neither brake will be actuated and reverse energization of the motor takes place to drive the frame in an opposite direction.

In FIG. 5D, however, the relationship between scanning frame and the gantry illustrates a situation where the dynamic braking of the motor fails and the brake mechanism 50b is engaged. Continued movement of the frame 14 causes the arm 115 to drive the cam 110 past the brake mechanism 50b causing contact between that mechanism's brake shoe 54 and the braking surface 52. The normal force between this brake shoe 54 and the surface 52 is such that movement stops with no more than 30° of additional rotation. Thus, FIG. 5D indicates a situation in which the frame has been brought to rest by the brake mechanism 50b.

In FIG. 5E opposite sense scanning motion (counterclockwise) has been initiated. The cam 110 remains stationary and the brake mechanism 50b remains in contact with the braking surface. The self-releasing aspect of the brake mechanism is experienced during counterclockwise rotation so that the motor 30 is able to drive the frame even though the brake pad 55 rides on the braking surface 52. By comparison of FIGS. 5D and 5E it is apparent that the frame 14 rotates approximately 270° before the arm 116 contacts the operator 114. When this happens the operator 114 and cam 110 begin to move.

Continued counterclockwise rotation of the frame moves the cam 110 past the brake mechanism 50b thereby retracting the brake shoe 54. Continued rotation occurs until a scan has been completed and dynamic braking initiated. A comparison of FIG. 5F and 5A indicates an identity of configuration for the frame and for the two mechanisms 50a, 50b.

FIG. 5G illustrates a situation in which the dynamic braking of the motor has again failed to bring the frame 14 to rest. The arm 116 drives the cam operator 114 so that the cam 110 passes the brake mechanism 50a. This brake mechanism is actuated and contact between its brake shoe and the friction surface terminates motion. Subsequent to actuation of the brake mechanism 50a, scanning motion is reversed and the cam 110 retracts the brake shoe of the mechanism 50a.

The disclosed brake has been illustrated with a degree of particularity in a fourth generation computed tomography setting. It is the intent, that the invention include all modifications and alterations embodied within the spirit or scope of the appended claims.

We claim:

1. A computed tomography scanner comprising
   a first structure including an X-ray source rotatably supported by a second structure such that relative rotation between the first and second structures causes X-ray scanning of a subject,
   detector means mounted to one of said first and second structures to detect X-rays passing through said subject; and
   a braking apparatus for stopping movement between said two structures, said braking apparatus including:
   brake means mounted to one of said first and second structures and having a brake pad which upon actuation of the brake means applies a braking force;
   means defining a brake pad contact surface coupled to a different one of said first and second structures than the brake means; and
   means for engaging said brake pad against the contact surface, said means for engaging including a cam surface, a brake actuator which initiates braking co-action between the contact surface and said brake pad in response to contact by said cam surface; and means for maintaining the force of engagement between the brake pad and contact surface.

2. The scanner of claim 1 wherein when the first and second structures relatively rotate in one direction a predetermined angular distance, motion is stopped and the direction of rotation reversed, said brake means comprising two brake shoes each having an associated brake pad and said means for engaging comprising two brake actuators, one for each brake shoe such that contact between said cam surface and a first of said actuators stops motion in one direction and contact between a second actuator and said cam surface stops motion in an opposite direction.

3. The computed tomography scanner of claim 1 where the brake pad is pivotally connected to said second structure by a lever arm for movement between a braking position and an non-braking position, where said contact surface comrprises part of said first structure and where the means for engaging comprising:
   biasing means for urging said brake pad toward the contact surface in the braking position; and
   means for retaining said brake pad in said non-braking position;
   said cam surface co-acting with said means for retaining in order to release said brake pad and allow said biasing means to urge said brake pad into said braking position.

4. The computed tomography scanner of claim 3 wherein said means for retaining includes a first contact pin extending beyond a surface of said means for retaining, and said cam surface engages said first pin to move said means for retaining and release said brake pad to said braking position.

5. The computed tomography scanner of claim 4 wherein said means for engaging includes a second pin which also co-acts with said cam surface to retract brake pad upon engagement of said retaining means.

6. The computed tomography scanner of claim 5 wherein said brake pad is biased to said braking position as the brake pad moves relative to said cam surface in one direction and said brake pad is retracted and held in said non-braking position as the brake pad moves in an opposite direction.

7. The computed tomography scanner of claim 3 where the biasing means comprises a compressed spring and wherein said lever arm forms an angle with respect to said braking surface which increases with wear of said brake pad to increase the force of co-action between the contact surface and brake pad as the biasing action of the spring decreases.

8. In a computed tomography scanner of the type where a source of X-rays scans a subject and irradiates an array of detectors, a method for braking scanning motion of said source comprising the steps of:
   causing rotation of a scanning structure to which the source of X-rays is coupled in a first direction by energizing an induction motor; said scanning structure including a friction surface that rotates with the scanning structure;
   biasing a brake pad toward said friction surface while holding said brake pad out of engagement with said friction surface;
   irradiating said subject with X-rays as motion occurs;
   arresting said motion by reverse energizing said motor to dynamically brake said scanning structure;
   sensing motion of said structure in said first direction, and
   releasing said brake pad into engagement with said friction surface in the event the reverse motor energization fails to stop said structure within a predetermined range of travel.

9. In a computed tomography scanner of a type where radiation from a source passes through a region of interest in a subject and is detected by one or more x-radiation detectors, apparatus comprising:

a stationary scanner gantry;

a rotatably mounted frame supported by said gantry, said frame having means for mounting at least said source for movement about a patient along a scanning plane relative to said gantry;

an annular bearing for rotatably supporting said frame, said bearing having a rotating, axially elongated race which defines a braking surface;

a motor for causing scanning movement between the frame and gantry; and a brake system for stopping said motion, said brake system having
(i) two separately actuatable brake shoes, one of said shoes for engaging said surface to stop relative motion in one direction and a second brake shoe for engaging said surface to stop scanning motion in an opposite direction;
(ii) a brake release mounted to said frame for movement relative to said two brake shoes for activating one brake shoe as the brake release rotates past said one brake shoe in one direction and for activating the second brake shoe as the brake release rotates in an opposite direction;

said brake release being rotatably supported by said frame to allow relative movement between the frame and said brake release; and
(iii) break release drive means coupled to the frame for movinging said brake release and frame in unison after a determined amount of relative motion between the frame and the brake release.

10. The scanner of claim 9 wherein the brake release comprises a cam surface for actuating said two brake shoes and a cam operator for co-acting with said actuator drive, said cam and cam operator being coupled to a rotatable ring supported by bearings and surrounding said patient scanning plane.

* * * * *